United States Patent [19]
Leiner et al.

[11] Patent Number: 5,952,491
[45] Date of Patent: Sep. 14, 1999

[54] METHOD OF DETERMINING AN ALKALI ION

[75] Inventors: Marco Jean Pierre Leiner, Graz, Austria; Huarui He, Alpharetta, Ga.; Andrei Boila-Göckel, Graz, Austria

[73] Assignee: AVL Medical Instruments, Schaffhausen, Switzerland

[21] Appl. No.: 09/085,218

[22] Filed: May 27, 1998

[30] Foreign Application Priority Data

May 30, 1997 [AT] Austria ........................................ 930/97

[51] Int. Cl.$^6$ ........................ C07D 419/02; G01N 21/64
[52] U.S. Cl. ............................ 540/467; 540/450; 436/74
[58] Field of Search ................................. 540/467, 450; 436/74

[56] References Cited

U.S. PATENT DOCUMENTS

| | | | |
|---|---|---|---|
| 4,774,339 | 9/1988 | Haugland et al. | 548/405 |
| 5,162,525 | 11/1992 | Masilamani et al. | 540/468 |
| 5,439,828 | 8/1995 | Masilamani et al. | 436/74 |
| 5,516,911 | 5/1996 | London et al. | 548/236 |

OTHER PUBLICATIONS

Bradshaw et al., Aza–Crown Macrocycles., 1993 John Wiley & Sons Inc., N.Y. (selected tapes).

J.R. Lakowicz, "Topics in Fluorescence Spectroscopy", vol. 4: Probe Design and Chemical Sensing, pp. 133–134 (Plenum Press, New York and London) (1994).

Frank Kastenholz, Inaugural Dissertation, University of Cologne, Fig. 32, p. 54 (1993).

R. Crossley, Zia Goolamali and Peter G. Sammes, "Synthesis and Properties of a Potential Extracellular Fluorescent Probe for Potassium", J. Chem. Soc. Perkin Trans. 2, pp. 1615–1622 (1994).

M.J.P. Leiner, P. Hartmann, "Theory and practice in optical pH sensing", Sensors and Actuators B, vol. 11, pp. 281–289 (1993).

A.P. de Silva, et al., Tetrahedron Letters, "A New Benzo–Annelated Cryptand and a Derivative with Alkali Cation–Sensitive Fluorescence", vol. 31, No. 36, pp. 5193–5196 (1990).

B. Dietrich, J.M. Lehn, J.P. Sauvage, J. Blanzart, "Syntheses et Proprietes Physiques De Systemes Diaza–Polyoxa–Macrobicycliques", Tetrahedron vol. 29, pp. 1629–1645 (1973). CA 99:177723h.

*Primary Examiner*—Richard L. Raymond
*Assistant Examiner*—Pavanaram K Sripada
*Attorney, Agent, or Firm*—Baker & Botts LLP

[57] ABSTRACT

The invention relates to a method of determining an alkali ion in a sample, wherein the alkali ion is contacted with a compound having a luminophoric moiety and an ionophoric moiety, which ionophoric moiety reacts with the alkali ion present in the sample, wherein the luminophoric moiety changes its luminescence properties, after which the luminescence is measured and the alkali ion determined utilizing the test reading, which method is characterized in that the compound utilized is a monoaza-crown ether of the general Formula I

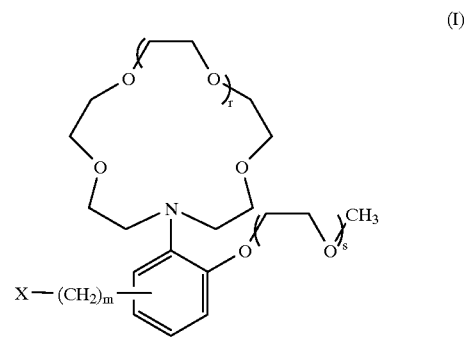

in which X is the luminophoric moiety, m is the number 0, 1 or 2, and r and s independently mean the numbers 0, 1 or 2.

6 Claims, 6 Drawing Sheets

METHOD OF DETERMINING AN ALKALI ION

BACKGROUND OF THE INVENTION

The present invention relates to a method of determining an alkali ion in a sample, wherein the alkali ion is contacted with a compound (=luminophore-ionophore) having a luminophoric moiety and an ionophoric moiety, which ionophoric moiety reacts with the alkali ion present in the sample, wherein the luminophoric moiety changes its luminescence properties, after which the luminescence is measured and the concentration or the activity of the alkali ion are deduced, i.e. the alkali ion is determined, utilizing the test reading. The invention also relates to monoaza-crown ethers capable of being used as luminophore-ionophores for determining an alkali ion.

A determination method of this type is based on the so-called "PET effect". This latter term denotes the transfer, induced by photons, of electrons (photoinduced electron transfer=PET) from the ionophoric moiety or ionophore, respectively, to the luminophoric moiety or luminophore, respectively, which leads to a decrease in the (relative) luminescence intensity and the luminescence decay time of the luminophore. Absorption and emission wavelengths, however, remain basically unaffected in the process (J. R. Lakowicz in "Topics in Fluorescence Spectroscopy", Volume 4: Probe Design and Chemical Sensing; Plenum Press, New York & London (1994)).

By the binding of ions to the ionophore, the PET effect is partly or completely inhibited, so that there is an increase in the luminescence of the luminophoric moiety. Hence, the concentration or the activity of the ion to be determined can be deduced by measuring the change in luminescence properties, i.e. luminescence intensity and/or luminescence decay time.

From U.S. Pat. No. 5,516,911, fluorescence indicators for determining intracellular calcium are known which carry fluorescent substituents capable of acting as optical indicators.

A method of the kind initially described is known from U.S. Pat. No. 5,439,828, wherein diaza-cryptands are utilized as the luminophore-ionophore, which diaza-cryptands have been functionalized as fluorophores with fluorescent coumarins and, depending on their structure, are selective for lithium, sodium and potassium ions, respectively. It is stated that these luminophore-ionophores can be used in sample media of neutral pH and are even the preferred choice in such systems.

Yet, research (Frank Kastenholz, Inaugural Dissertation, University of Cologne, 1993, FIG. 32, p. 54) has shown that in the physiological pH range the fluorescence signal depends significantly on the pH of the sample and increases considerably with decreasing pH, even from pH 7.4 onwards. This affects the accuracy of a determination carried out in a biological sample. Moreover, the compounds that are being used have the added disadvantage that the employed coumarins show absorption wavelengths of about 336 nm and hence cannot be excited by commercial LEDs.

These disadvantages also apply to the luminophore-ionophores mentioned in U.S. Pat. No. 5,162,525.

From Tetrahedron Letters, Volume 31, No. 36, pp. 5193–5196 (1990), diaza-cryptands are known in which the two nitrogen atoms are bound to a respective aromatic ring each, i.e. are aryl nitrogens and aniline-type nitrogens, respectively. Research conducted by the applicant has shown that these diaza-cryptands are not suited for determining potassium ions if they are present in the physiological range of concentration and at physiological pH values of the blood (7.0–7.6).

SUMMARY OF THE INVENTION

The present invention therefore has as its object to improve the known process or make available luminophore-ionophores which lack significant dependence of the luminescence properties on the pH value of the sample at physiological pH values and thus are suited for determination in biological samples.

Further, the method of the invention is to be particularly well suited for practice in the presence of physiological concentrations of alkali ions, i.e. it should exhibit a strong dependence of the luminescent signal on the concentration of the alkali ion being determined.

In the method initially described, this object is achieved in that the compound (=luminophore-ionophore) utilized is a monoaza-crown ether of the general Formula I (I)

in which X is the luminophoric moiety, m is the number 0, 1 or 2, and r and s independently mean the numbers 0, 1 or 2.

The monoaza-crown ethers showing the above general Formula I are novel. These novel luminophore-ionophores have been found to be very useful for determining alkali ions at physiological pH values and at physiological concentrations.

The monoaza-crown ethers of the invention are particularly useful for determining sodium ions in the concentration range between 110 and 180 mmol/l.

Without being bound to a specific theory, it is assumed that the advantageous properties of the monoaza-crown ethers of the invention are due to the fact that the nitrogen is an aromatic nitrogen.

Suitable luminophoric moieties X would be all those moieties by which in combination with the ionophoric moiety a PET effect can be achieved. A great number of moieties is known from literature which in combination with the ionophore give a PET effect or in principle are suited for this purpose. By coupling these known moieties to the benzene ring of the general Formulae I and II, new compounds are obtained which may be examined by the man skilled in the art in order to find out whether a PET effect can be obtained. Coupling may be in a position ortho to the nitrogen, in its two meta positions and in para position. The para position is the preferred position.

Those skilled in the art will be aware that in order for a PET effect to materialize it is essential in particular that the electron donor of the ionophoric moiety be electronically decoupled from the electronic system of the luminophoric moiety. As is well known in the art, such electronic decoupling of the ionophoric and luminophoric moieties may be achieved in that the two moieties present are separated either by a spacer group, i.e. the $(CH_2)_m$ chain with m>0 or—if m=0—by a virtual spacer (f.i. by pivoting the plane of the luminophoric moiety to the plane of the benzene ring). Hence, the function of the spacer is to oppose conjugation of the electron system of the ionophoric moiety with the electron system of the luminophoric moiety.

Electronic decoupling can be recognized f.i. from the fact that there is no significant change concerning the wavelengths of the absorption and emission spectra.

For determining sodium ions there is preferably utilized a monoaza-crown ether of the general Formula I in which r and s mean the numbers 1 and 0, respectively.

Further, for determining potassium ions there is preferably utilized a monoaza-crown ether of the general Formula I in which r and s mean the numbers 2 and 1, respectively.

The luminophoric moiety X in the general Formula I preferably
is an amino-naphthalimide group of the general Formula II (II)

in which one of $R_1$, $R_2$, $R_3$, $R_4$, $R_5$ and $R_6$ is a group —NH— through which X is bonded to the group —$(CH_2)_m$— of the above-recited compound of the general Formula I and the remainder and $R_7$ are each independently hydrogen, a lipophilic or hydrophilic group or a reactive group for coupling to a polymer, or is a xanthenone group of the general Formula III (III)

in which one of $R_8$, $R_9$, $R_{10}$, $R_{11}$, $R_{12}$, $R_{13}$, $R_{14}$, and $R_{15}$ represent a chemical bond through which X is bound directly (m=0) to the ionophoric moiety of the above-recited compound of the general Formula I and the remainder represent —OH, —$OR_{16}$, in which $R_{16}$ is a hydrophilic or a lipophilic group, —O—$R_{17}$—G, in which $R_{17}$ is a hydrophilic or a lipophilic group and G a reactive group for coupling to a polymer, or —$(CH_2)_n$—COOH, in which n is a number between 0 and 17.

It is preferred that in the general Formula II $R_3$ or $R_4$ be the group —NH— through which the luminophoric moiety is bound to the group —$(CH_2)_m$— of the above-mentioned general Formula I.

It is further preferred that in the general Formula III $R_{12}$ be a chemical bond through which the luminophoric moiety is bound directly (m=0) to the ionophoric moiety of the above-mentioned general Formula I.

Suitable lipophilic groups would f.i. be substituted and unsubstituted alkyl groups and alkoxy groups having up to 20 C atoms.

Suitable hydrophilic groups would f.i. be alkyl groups having 1–17 C atoms and carrying at least one hydroxyl group and/or functional groups which at the pH of the measuring solution are present in a dissociated condition, such as f.i. carboxylic acids, sulfonic acids and phosphoric acids.

Reactive groups for coupling to aminofunctionalized polymers, f.i. aminocellulose and aminofunctional polyacrylamides, are known f.i. from U.S. Pat. No. 4,774,339, Table 4.

These above-recited luminophoric moieties, which are preferably utilized, may be excited using light of a wavelength of >450 nm.

The compounds of the invention for determining the alkali ions may be added to the sample solution in dissolved condition. However, they may also be components of a sensor, where they may be embedded in a layer formed f.i. from a hydrogel, as will be described hereinbelow with reference to FIG. 1.

BRIEF DESCRIPTION OF THE DRAWINGS

Further objects and advantages will be more fully appreciated from a reading of the detailed description when considered with the accompanying drawings wherein.

DETAILED DESCRIPTION OF THE PREFERRED EMBODIMENTS

The invention further relates to a monoaza-crown ether of the general Formula I in which X is the luminophoric moiety and in particular has the meaning set forth hereinabove, m is the number 0, 1 or 2, and r and s independently mean the numbers 0, 1 or 2.

In the following, the invention will be described in more detail by means of examples, wherein the synthesis and properties of some monoaza-crown ethers which are preferably used will be explained. Other compounds in accordance with the invention can be prepared in analogous manner by the person skilled in the art.

1. Synthesis of the Monoaza-Crown Ethers of the Invention 1.1. Synthesis of the ionophoric moiety of the monoaza-crown ethers of the invention (FIG. 1)

Figure 1:
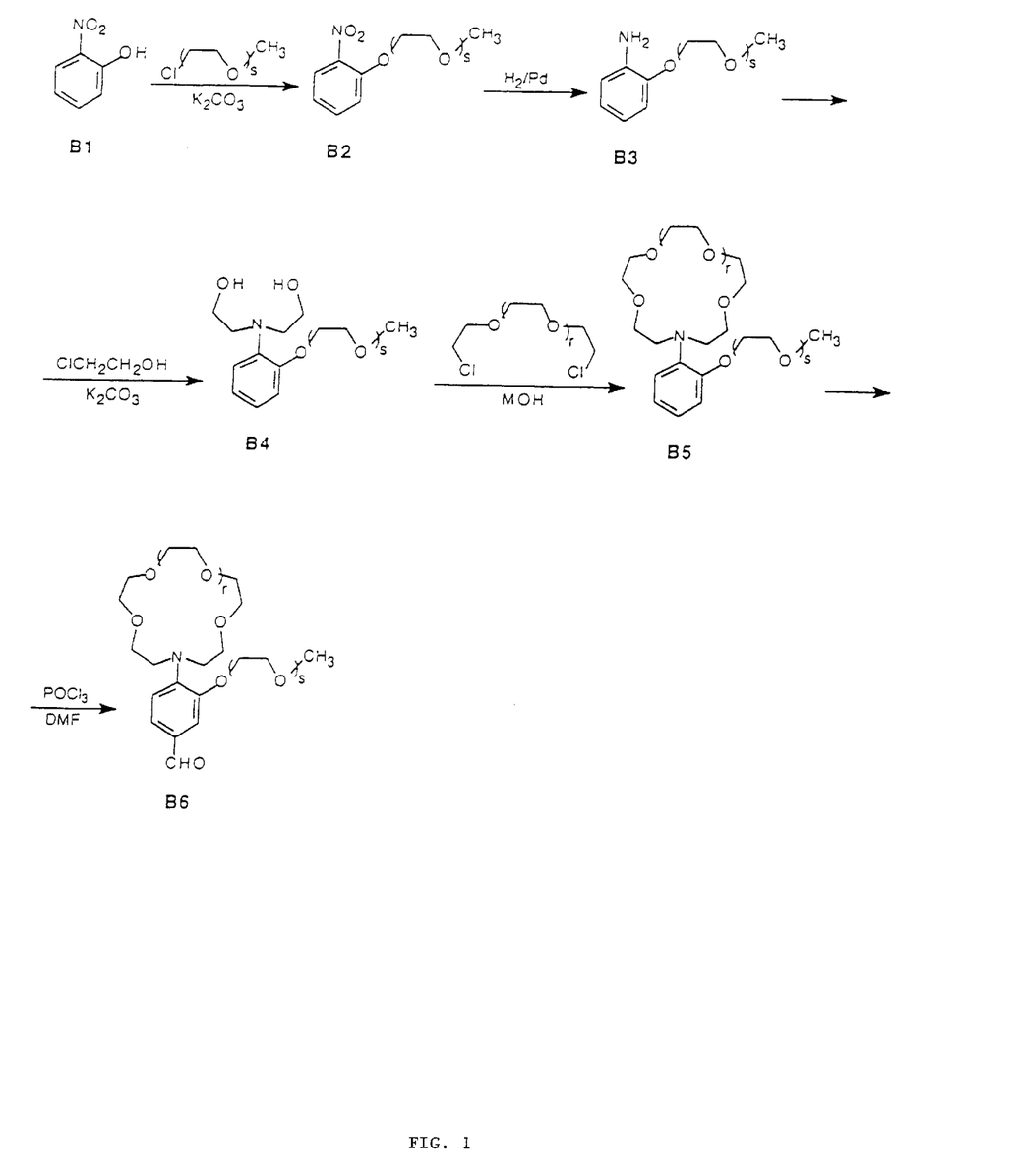
FIG. 1 is an illustration of a synthetic pathway for the ionophoric moiety of a monoaza-crown ether in accordance with the invention.

The synthetic pathway for the ionophoric moiety of the monoaza-crown ethers of the invention is represented generally in FIG. 1

General Process (FIG. 1)

The synthesis of monoaza-crown (lariat) ethers with side-arms was through two main steps: alkylation and cyclization. It was feasible to alkylate 2-nitrophenol B1 in dimethylformamide in the presence of $K_2CO_3$ using chloroethyl-alkoxyethers of different chain lengths (s=0, 1, 2). The resulting nitro compounds B2 were hydrated to obtain amines B3, followed by alkylation of the amino group in chloroethanol with $K_2CO_3$ as the base to obtain the 2-[N,N-bis (2-hydroxyethylaminophenyl-alkoxyethyl-ethers B4 (s=0, 1, 2). These bis-hydroxy compounds B4 were cyclized with ethylglycol-dichloroethyl ethers (r=0, 1, 2) in dioxane containing alkali hydroxide to obtain the lariat ethers B5 (r=0, 1, 2; s=0, 1, 2). These ethers B5 (phenylaza-crown ethers) were formylated to obtain the intermediate products B6 (r=0, 1, 2; s=0, 1, 2).

Description of individual reaction steps of FIG. 1

N,N-bis (2-hydroxyethyl)-2-methoxyaniline B4 (s=0):

452 g (4 mol) of o-anisidine were dissolved in 1932 g (24 mol) 2-chloroethanol and heated at 80° C. for 15 min. Subsequently, 608 g (4.4 mol) $K_2CO_3$ were added slowly in order to keep the temperature below 110° C. (exothermal reaction). The mixture was heated at 95° C. for 22 hours and was cooled down. About 800 ml unreacted chloroethanol were evaporated and the residue diluted with 1 l water and extracted twice with 1 l chloroform. The extract was washed 5 times with 1.5 l water and dried over $K_2CO_3$. The solvent was evaporated, wherein 404 g (yield: 48%) of light-brown oil were obtained. The thin-layer chromatogram showed a purity of about 95%.

$^1$H NMR (CDCl$_3$), δ (ppm): 3.18 (t, 4H), 3.50 (t, 4H), 3.60 (m, 2H), 3.82 (s, 3H), 6.90 (m, 2H), 7.10 (m, 1H), 7.19 (m, 1H).

2-methoxyphenylaza-15-crown-5 B5 (s=0, r=1):

This step was carried out based on J. P. Dix and F. Vögtle, Chem. Ber. 113, 457–470 (1980).

403 g (1.91 mol) B4 (s=0) were dissolved in 2210 ml dioxane and heated at 80° C. for 20 min. Subsequently, 168 g (4.20 mol) ground NaOH were slowly added within 3 hours. The temperature was raised to 95° C. when 300 ml (1.93 mol) bis (2-chloroethoxyethane) were added in one portion. Thereafter the reaction mixture was heated at 95° C. for 30 hours. After filtering the hot mixture the solvent was evaporated. The residue was treated with a solution of 234 g (1.91 mol) NaClO$_4$ in 640 ml methanol. The mixture was stirred for 30 min at 60° C. and was concentrated to about 300 ml. 860 ml ethylacetate were added, followed by stirring at room temperature for 20 min. The mixture was subsequently allowed to stand at room temperature for 2 hours.

The resulting precipitate was filtered, washed twice with 200 ml ethyl acetate and dried at room temperature for 30 min, wherein 199 g aza-crown sodium perchlorate complex were obtained as a soft white powder. This latter powder was dissolved in a mixture of 600 ml dichloromethane and 600 ml water, and the aqueous phase was again extracted with 400 ml dichloromethane. The organic layers were united, washed 8 times with 600 ml deionized water and dried over Na$_2$SO$_4$. The dichloromethane was evaporated, wherein 100.4 g of light-brown oil (yield: 16%) were obtained.

$^1$H NMR (CDCl$_3$), δ (ppm): 3.49 (t, 4H), 3.68 (t, 16H), 3.82 (s, 3H), 6.88 (m, 3H) 7.12 (m, 1H).

4-formyl-2-methoxyphenylaza-15-crown-5 B6 (s=0, r=1):

100 g (308 mml) B5 (s=0, r=1) were dissolved in 145 ml (1850 mmol) dimethylformamide in a 500 ml three-necked flask and cooled down to −5° C. 57.4 ml (616 mmol) POCl$_3$ were added dropwise in an addition funnel. The internal temperature of the flask was not allowed to rise above 5° C. This was followed by 16 hours of stirring at room temperature, pouring onto 500 g ice and adjustment to pH 7 with saturated aqueous K$_2$CO$_3$ solution. The solution was extracted twice with 500 m chloroform. The chloroform phase was washed twice with 500 ml water, then dried over 100 g MgSO$_4$ for 1 hour. The solvent was evaporated, wherein 85 g of light-yellow oil were obtained which crystallized when allowed to stand at room temperature overnight. Recrystallization from ethylacetate/hexane (1:4) yielded 56 g light-orange crystals (yield: 51%). $^1$H NMR (CDCl$_3$), δ (ppm):3.68 (t, 16H), 3.78 (t, 4H), 3.82 (s, 3H), 7.05 (m, 1H), 7.28 (m, 2H), 9.78 (s, 1H).

Figure 2:
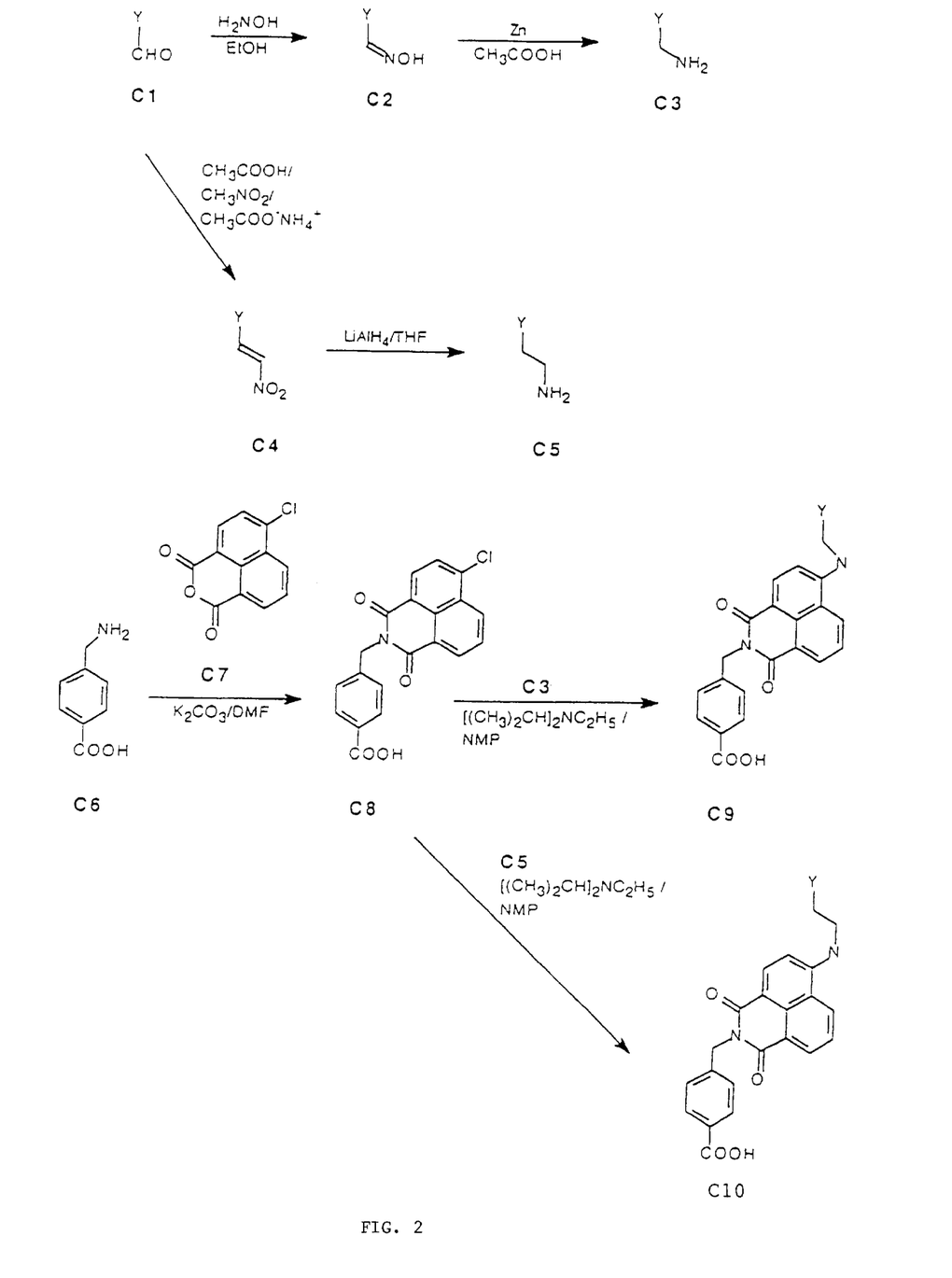
FIG. 2 is an illustration of a synthetic pathway for a monoaza-crown ether in accordance with the invention in which the luminophoric moiety is an aminonaphthalimide group.
Figure 3:
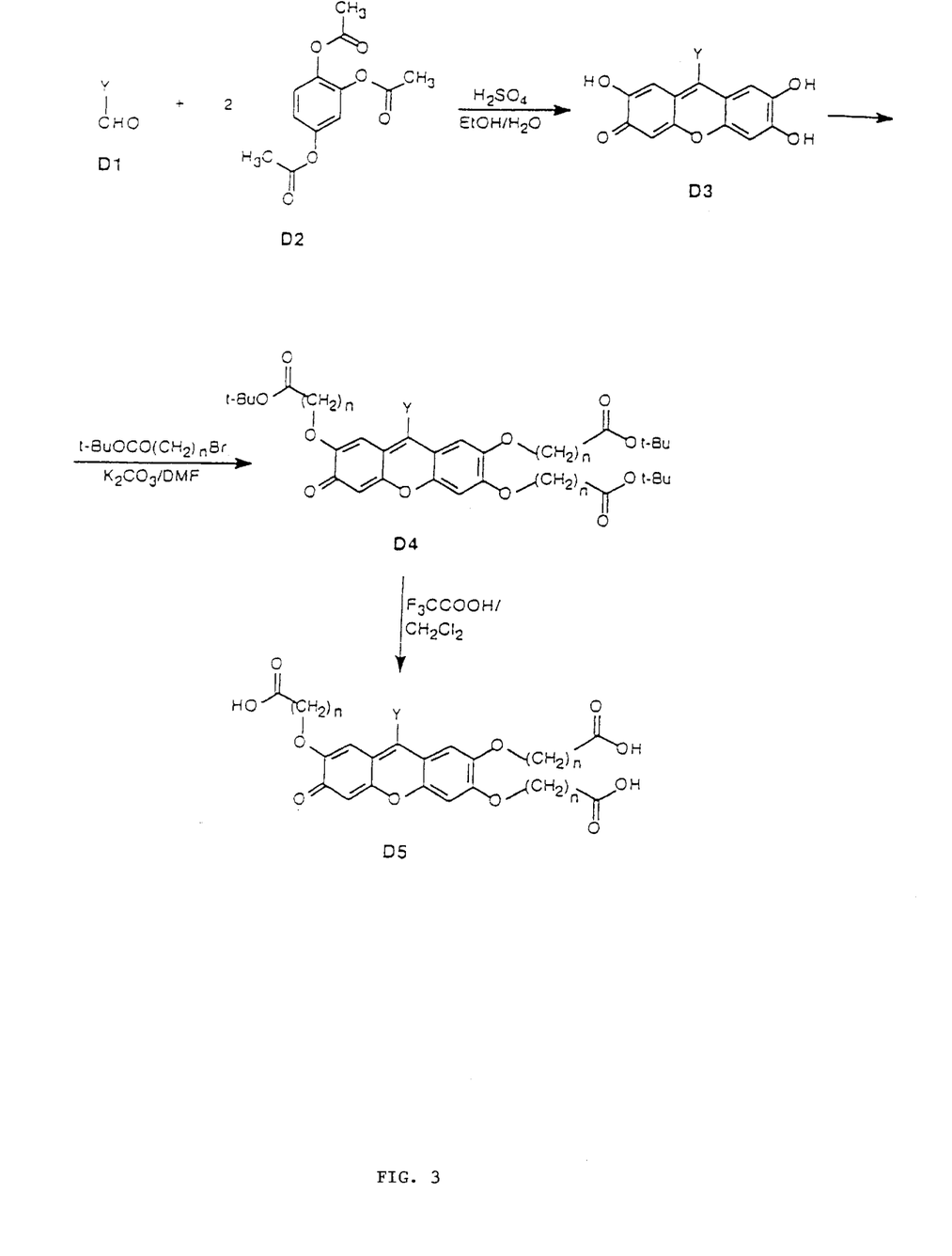
FIG. 3 is an illustration of a synthetic pathway for a monoaza-crown ether in accordance with the invention in which the luminophoric moiety is a xanthenone group.

1.2 Preparation of the monoaza-crown ethers of the invention (FIGS. 2 and 3)

The preparation of the monoaza-crown ethers of the invention is exemplified in FIGS. 2 and 3 for two luminophoric moieties (aminonaphthalimide and xanthenone, respectively), wherein "Y" in each case represents the ionophoric moiety.

General process of FIG. 2 (the luminophoric moiety is an aminonaphthalimide group)

Compounds of the invention having a single CH$_2$ group as a spacer between the luminophoric and the ionophoric moiety were prepared in that, first, the compound C1, which may f.i. be the compound B6 (FIG. 1), in which "Y" represents B5, was converted to the oxime C2 and by means of Zn in acetic acid was reduced to obtain the amine C3. Coupling to the luminophoric moiety in order to prepare the compound C9 of the invention is shown schematically in FIG. 2 by means of the aminonaphthalimide C8 prepared by reacting C6 with C7 in dimethylformamide in the presence of K$_2$CO$_3$.

Compounds of the invention having two CH$_2$ groups acting as a spacer between the luminophoric and the ionophoric moiety were prepared in that, first, the compound C1 was reacted to the compound C4 with a great excess of nitromethane in the presence of ammonium acetate, the compound C4 was subsequently reduced by means of LiAlH$_4$ in THF to obtain the amine C5. Coupling to the aminonaphthalimide C8 to prepare the compound C10 is also shown schematically in FIG. 2.

Description of individual reaction steps of FIG. 2

4-oximyl-2-methoxyphenylaza-15-crown-5 C2 (s=0, r=1):

To a solution of 80 g (226 mmol) B6 (s=0, r=1) in 550 ml ethanol, a solution of 20.4 g (293 mmol) hydroxylamine hydrochloride and 20.4 g (146 mmol) K$_2$CO$_3$ in 550 ml water was added. The mixture was stirred for 16 hours at room temperature and for 3 hours at 70° C. After this, ethanol was evaporated and the residue dissolved in a mixture of 500 ml chloroform and 300 ml water. The aqueous layer was extracted with 500 ml chloroform. The chloroform extracts were united and washed twice with 500 ml water and dried over K$_2$SO$_4$. The solvent was evaporated, wherein 80.1 g of yellow oil were obtained (yield: 96%).

4-aminomethyl-2-methoxyphenylaza-15-crown-5 C3 (s=0, r=1):

To a solution of 45 g (122 mmol) C2 (s=0, r=2) in 450 ml acetic acid, 78 g (1180 mmol) zinc dust were slowly added under cooling with ice water. This suspension was stirred for 18 hours at room temperature and for 3 hours at 70° C., filtered and washed three times with 200 ml ethanol. The solvent was evaporated and the obtained oil was dissolved in a mixture of 300 ml chloroform and 300 ml water and with 6 n KOH was adjusted to pH 12. The aqueous layer was washed with 500 ml chloroform. The united chloroform extracts were washed twice with 500 ml water and dried over K$_2$CO$_3$. The solvent was evaporated, wherein 35.2 g of brownish-yellow oil (yield: 78%) were obtained.

The thin-layer chromatogram showed a purity of about 70% and the spot turned bluish-violet upon treatment with ninhydrine. This amine was used directly for the subsequent step, without further purification.

4-nitroethylenyl-2-methoxyphenylaza-15-crown-5 C4 (s=0, r=1):

18.8 g (50 mmol) B6 (s=0, r=1), 38.5 g (500 mmol) ammonium acetate were suspended in 100 ml acetic acid and stirred for 10 min at room temperature. Then, 59.4 ml (1100 mmol) nitromethane were added. The mixture was heated at 60° C. for 5 hours and was subsequently poured into ice water. The obtained crystals were filtered off, washed with water and dried in an exsiccator using P$_2$O$_5$, wherein 11.9 g dark red needles (yield: 60%) were obtained.

$^1$H NMR (CDCl$_3$), δ (ppm): 3.68 (t, 16H), 3.78 (t, 4H), 3.82 (s, 3H), 6.88 (m, 1H), 7.08 (m, 2H), 7.45 (d, 1H), 7.85 (d, 2H).

4-aminoethyl-2-methoxyphenylaza-15-crown-5 C5 (s=0, r=1):

To 200 ml tetrahydrofuran in a 500 ml three-necked flask, 3.8 g (100 mmol) LiAlH$_4$ were slowly added. Subsequently, 4.0 g (10 mmol) C4 (s=0, r=1) in 50 ml tetrahydrofuran were added dropwise within 2 hours. The mixture was heated under reflux for 4 hours and subsequently was cooled down in an ice bath. 6 n KOH was added to destroy unreacted LiAlH$_4$. Then, filtration was carried out, the solvent was evaporated and the residue dissolved in 150 ml chloroform, washed twice with 150 ml water, dried over 15 g K$_2$CO$_3$ and the solvent was evaporated, wherein 4.9 g of orange-colored oil (yield: 125%) were obtained.

The thin-layer chromatogram showed a purity of about 80% and the spot turned bluish-violet when treated with ninhydrine. This amine was then used directly, without further purification.

4-chloro-N-(4-carboxyphenylmethyl)-1,8-naphthalimide C8:

46.4 g (200 mmol) 4-chloro-1,8-naphthalenic acid anhydride C7, 30.2 g (200 mmol) 4-aminomethylbenzoic acid C6 and 13.8 g (100 mmol) K$_2$CO$_3$ were suspended in 2 l dimethylformamide, then were stirred for 16 hours at room temperature and for 6 hours at 60° C. The mixture was subsequently poured into 4 l water and adjusted to pH4 using 6 n HCl. The obtained precipitate was filtered off and dried for 18 min at 60° C., wherein 36 g of off-white powder (yield: 51%) were obtained.

4-{4'-[4"-C-(aza-15-crown-5)-3"-methoxyphenylmethylamino]-1',-8'-naphthalimidylmethyl}-benzoic acid C9:

3.68g (10 mmol) C3, 5.05 g (70%, 10 mmol) C8 (r=1, s=0) and 3.25 g (25 mmol) diisopropyl ethyl amine were suspended in 25 ml N-methylpyrrolidinone and heated at 110° C. for 15 hours, subsequently were cooled down and poured into 475 ml 2% aqueous acetic acid. The obtained precipitate was filtered off and washed twice with 100 ml water, dried for 18 hours in an exsiccator using P$_2$O$_5$, wherein 4.6 g of brownish yellow solid was obtained which was a mixture of C3 and the product.

This solid was dissolved in a hot mixture of chloroform/methanol (3:1). This was followed by filtration. The filtrate was fed to a column packed with 60 g silica gel 100, and a rinsing operation with chloroform/methanol (3:1) was carried out to remove unreacted C3. This was followed by rinsing with chloroform/methanol (3:1), containing 1% acetic acid, to obtain 0.58 g (yield: 8.5%) of the desired product.

$^1$H NMR (D$_3$CS (=O) CD$_3$), δ (ppm): 3.25 (t, 4H), 3.50 (t, 16H), 3.75 (s, 3H), 4.15 (t, 1H), 4.58 (d, 2H), 5.25 (s, 2H), 6.78 (d, 1H), 6.88 (m, 2H), 7.38 (d, 2H), 7.55 (m, 2H), 7.82 (d, 2H), 8.20 (d, 2H), 8.50 (m, 1H), 8.80 (d, 1H).

C$_{42}$H$_{49}$N$_3$O$_{13}$ Calculated for diacetate: C 62.75; H 6.14; N 5.23. Found: C 62.37; H 6.09; N 5.12.

4-{4'-[4"-C-(aza-15-crown-5)-3"-methoxyphenylethylamino]-1',-8'-naphthalimidylmethyl}-benzoic acid C10:

1.85 g (5 mmol) C5, 2.62 g (80%, 10 mmol) C8 (r=1, s=0) and 1.63 g (12.5 mmol) diisopropyl ethyl amine were suspended in 12.5 ml N-methylpyrrolidinone and heated at 110° C. for 15 hours. This was followed by cooling and pouring into 238 ml aqueous 2% acetic acid. The resultant precipitate was filtered off and washed twice with 50 ml water, dried for 18 hours in an exsiccator using P$_2$O$_5$, wherein 1.8 g of brownish-yellow solid were obtained which solid was a mixture of C5 and the product.

This solid was dissolved in 100 ml of a hot mixture of chloroform/methanol (9:1). This was followed by filtration. The filtrate was fed to a column packed with 180 g silica gel 100. Rinsing with chloroform/methanol (9:1) was carried out to remove unreacted C5 and this was followed by rinsing with chloroform/methanol (3:1), containing 1% acetic acid, to obtain 0.52 g (14.9%) of the desired product.

$^1$H NMR (D$_3$CS (=O) CD$_3$), δ (ppm):2.90 (t, 2H), 3.25 (t, 4H), 3.50 (t, 16H), 3.60 (t, 2H), 3.75 (s, 3H), 4.45 (t, 1H), 5.25 (s, 2H), 6.78 (d, 1H), 6.88 (d, 1H), 6.95 (d, 1H), 7.25 (m, 2H), 7.65 (d, 1H), 7.80 (d, 2H), 7.95 (t, 1H), 8.25 (d, 1H), 8.45 (d, 1H), 8.75 (d, 1H).

FABMS (70 eV, m-nitrobenzylalcohol dispersion with LiJ): 711 (15%), (M+2Li—H); 670 (31%), (M-CO$_2$-H+2Li); 313 (100%) (phenylaza-crown+Li).

Process of FIG. 3 (the luminophoric moiety is a xanthenone group)

8-[4'-C-(aza-15-crown-5)-3'-methoxyphenyl]-2,3,7-trihydroxyfluor-6-one D3 (r=1, s=0):

To a suspension of 6.51 g (25 mmol) triacetoxybenzene in 60 ml 50% (v/v) ethanol, 5 ml concentrated $H_2SO_4$ were added dropwise, stirred for 10 min, and then 4.42 g (12.5 mmol) B6 (s=0, r=1) were added in one portion. The resultant suspension was heated at 80° C. for 22 hours. The bulk of the ethanol was subsequently found to have evaporated. The residue was diluted with 50 ml water, was adjusted to pH 5 with 25% tetramethylammonium hydroxide and allowed to stand overnight. The liquid was decanted and the red solid was washed 3 times with 50 ml water and triturated three times with 50 ml methanol. The solvent was evaporated, wherein 4.2 g (33.5%) of red foam were obtained, which foam was utilized directly in the subsequent step.

8-[4'-C-(aza-15-crown-5)-3'-methoxyphenyl]-2,3,7-tri-t-butoxycarbonylmethylfluor-6-one D4 (r=1, s=0):

1.14 g (2 mmol) D3 with r=1 and s=0, 1.00 g (6 mmol) KJ, 1.76 g (9 mmol) $K_2CO_3$ and 1.76 g (9 mmol) t-butylbromoacetate were suspended in 10 ml dimethylformamide and heated at 110° C. for one hour. The mixture was cooled down and diluted with 90 ml water. This solution was extracted twice with 80 ml chloroform, washed with 160 ml water 3 times and dried over $K_2CO_3$. The solvent was evaporated, wherein 1.50 g of dark red gum-like substance were obtained. This crude product was purified with silica gel 100 and with chloforn/methanol (9:1), wherein 0.95 g of red oil (yield: 59%) were obtained.

8-[4'-C-(aza-15-crown-5)-3'-methoxyphenyl]-2,3,7-tricarboxymethylfluor-6-one D5:

0.93 g (1.1 mmol) D3 (r=1, s=0) were dissolved in 2.5 ml dichloromethane, and 0.5 ml trifluoroacetic acid (TFA) were added. The mixture was heated at 40° C. for 4 hours. Subsequently, the solvent and TFA were evaporated and the residue was dissolved in 10 ml methanol, whereupon the methanol was evaporated. This procedure was repeated 3 times so as to completely remove the TFA, wherein 0.87 g of red gum-like substance were obtained. This gum-like substance was utilized directly for the immobilization described hereinbelow.

2. Luminescence Properties of the Monoaza-Crown Ethers of the Invention

FIGS. 4 to 8 show the luminescence properties of compounds of the invention in solution and immobilized on cellulose as a function of the given concentration of alkali ions. The ordinates of the represented diagrams indicate the respective relative luminescence intensities.

Figure 4:
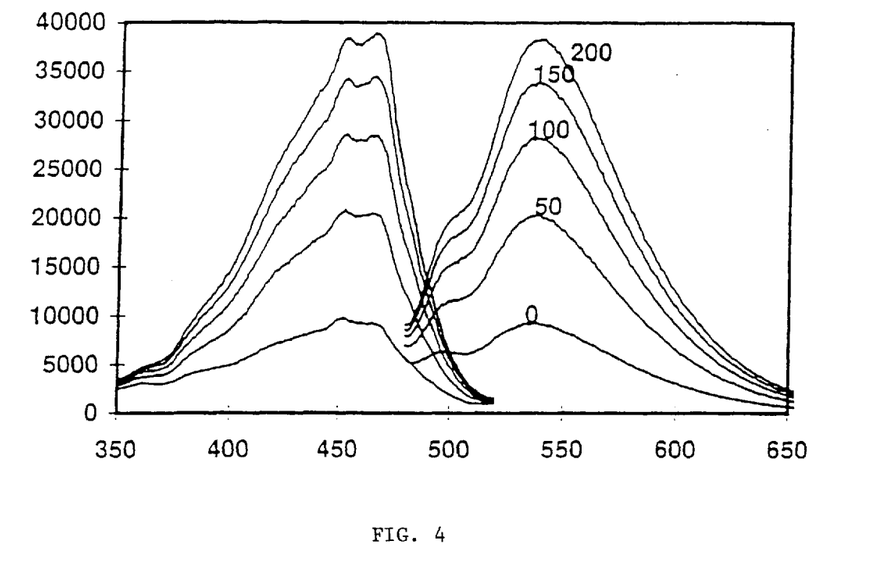
FIG. 4 is a graph illustrating the luminescence of a monoaza-crown ether in accordance with the invention versus sodium concentration.

2.1. FIG. 4

FIG. 4 shows the relative luminescence intensity of the monoaza-crown ether C9 of the invention in aqueous solution ($2 \times 10^5$ mol/l; 30 mmol/l tris/HCl buffer; $CO_2$-free; pH: 7.4; 37° C.) as a function of the wavelength (nm; abscissa) at the following Na concentrations: 0, 50, 100, 150 and 200 mmol/l.

The excitation spectra (on the left) and the emission spectra (on the right) were determined using a commercial spectrofluorometer.

Figure 5:
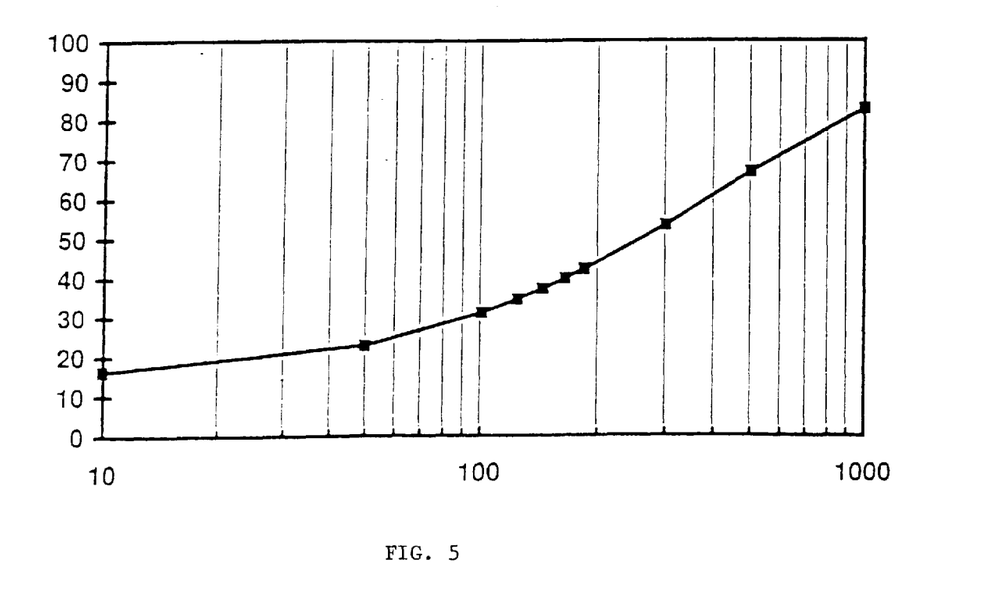
FIG. 5 is a graph illustrating the relative luminescence intensity of a $C_9$ monoaza-crown ether in accordance with the invention covalently immobilized on aminocellulose.

2.2. FIG. 5

FIG. 5 shows the relative luminescence intensity of the monoaza-crown ether C9 of the invention which was covalently immobilized on aminocellulose.

Immobilization on cellulose fibers (aminomodified) was done as follows:

0.03 mmol of the crown ether C9, 0.06 g (0.3 mmol) N,N-dicyclohexyl-1,3-carbodiimide, 0.4 g (0.3 mmol) N-hydroxysuccinimide and 5 g activated cellulose (prepared in accordance with SU-A-1,028,677, CA 99:177723h) were suspended in 2 ml dimethylformamide for 20 hours. The cellulose was then filtered off, washed 5 times with 5 ml dimethylformamide, 5 ml water, twice with 5 ml 0.2 n HCl, 5 ml water, twice with 5 ml 0.2 n NaOH, 10 times with 5 ml water, twice with 5 ml acetone and twice with 5 ml ether, and was dried for 16 hours at room temperature. Subsequently, the cellulose was sieved (25 $\mu$m).

Sensor discs were produced in the following manner:

0.25 g sieved (25 $\mu$m) aminocellulose fibers with immobilized crown ether C9 were suspended in 4.75 g 10% hydrogel D4 (Tyndale Plains-Hunter LTD. Ringoes, N.J. 08551) in 90% ethanol-water for 16 hours. The resulting homogenous dispersion was applied to a polyester foil (Melinex foil, ICI America) up to a dry density of 10 $\mu$m. This foil was coated over with 3% activated carbon in 10% D4 hydrogel up to a dry density of 5 $\mu$m, whereupon a small disc 2.5 cm in diameter was cut out. This disc was left in the buffer for at least 16 hours for activation.

A method of cutting and measuring sensor discs was described by M. J. P. Leiner and P. Hartmann in Sensors and Actuators B, 11 (1993), 281-189 ("Theory and Practice in optical pH sensing").

Figure 9:
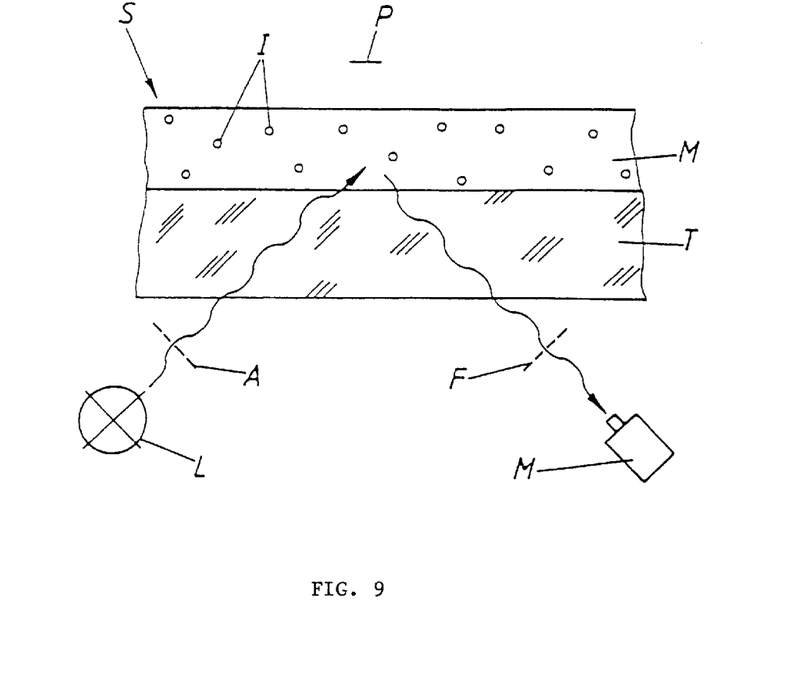
FIG. 9 is a schematic of a luminescence measuring system in accordance with the invention.

The sensor disc thus obtained was used in the measuring set-up represented schematically in FIG. 9.

In FIG. 9, the reference character S denotes a portion of the sensor disc. The compound immobilized on the cellulose fibers is denoted by I and is present in the hydrogel (layer M). This layer M is permeable to ions and is carried by a carrier T permeable to excitation and measuring radiation, which is a transparent foil.

According to the invention, the compound I can be bound to the ion-permeable matrix directly in a covalent manner or it can be present in the matrix in physically dissolved condition.

For measurement, the sensor disc was introduced into a thermostatted through-flow cell impervious to light and was contacted with samples P having different concentrations of sodium ions.

The optical measuring system consisted of a blue LED as the light source A, a photodiode M as the detector, optical filters A and F for selecting the wavelengths, a fiber-optic arrangement for conducting the excitation light into the polymer M and for conducting the emission light to the photodetector M as well as a device for electronic signal processing (not illustrated). At the excitation end there was utilized an interference filter (peak transmission at 480 nm) and at the emission end a 520 nm cut-off filter.

FIG. 5 shows the relative luminescence intensity (ordinate) as a function of the concentration of sodium ions (10, 50, 100, 124, 144, 164, 184, 300, 500 and 1000 mmol/l; logarithmic scale).

The measuring medium was 30 mmol/l tris/HCl buffer, $CO_2$-free; pH: 7.4; 37° C.

Figure 6:
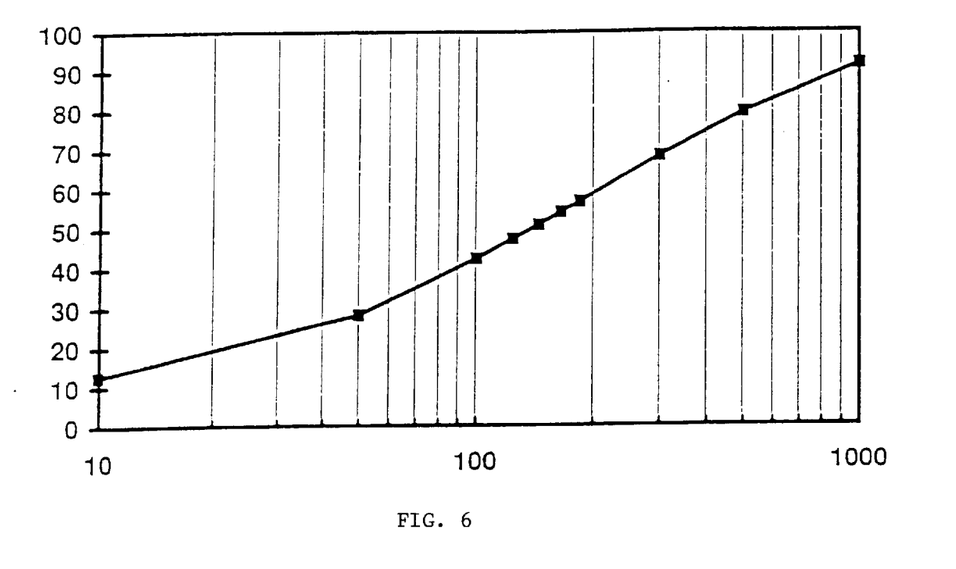
FIG. 6 is a graph illustrating the relative luminescence intensity of a $C_{10}$ monoaza-crown ether in accordance with the invention covalently immobilized on aminocellulose.

FIG. 6

FIG. 6 was obtained in a manner analogous to FIG. 5 but utilizing the monoaza-crown ether C10 instead of the monoaza-crown ether C9.

Figure 7:
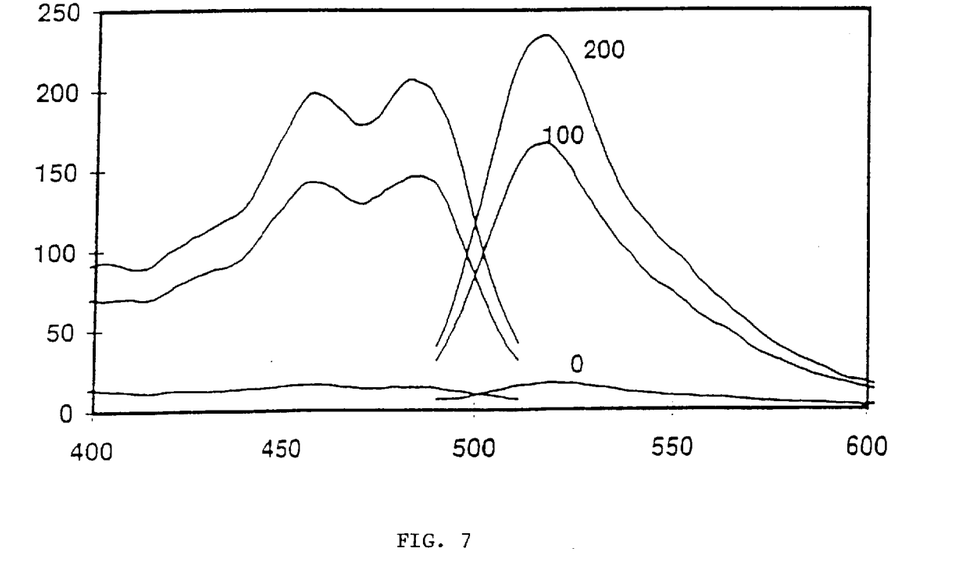
FIG. 7 is a graph illustrating the luminescence of a $D_5$ monoaza-crown ether in accordance with the invention versus sodium concentration.

FIG. 7

FIG. 7 shows the relative luminescence intensity of the monoaza-crown ether D5 of the invention in aqueous solution ($2 \times 10^{-5}$ mol/l; 30 mmol/l tris/HCl buffer; $CO_2$-free; pH: 7.4; 37° C.) as a function of the wavelength (nm; abscissa) at the following Na concentrations: 0, 100 and 200 mmol/l.

Figure 8:
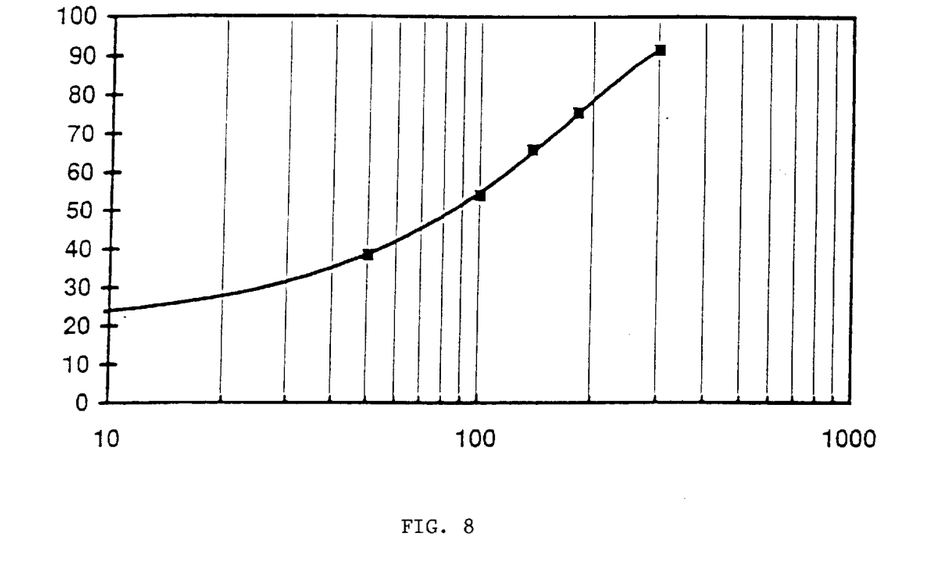
FIG. 8 is a graph illustrating the relative luminescence intensity of an $F_5$ monoaza-crown ether in accordance with the invention covalently immobilized on aminocellulose.

FIG. 8

FIG. 8 was obtained in a manner analogous to FIG. 5 but utilizing the monoaza-crown ether F5 instead of the monoaza-crown ether C9 and with the Na ion concentrations being 1, 50, 100, 138, 182 and 300 mmol/l.

We claim:

1. Method of determining an alkali ion in a sample comprising the steps of:
providing a compound having a luminophoric moiety and an ionophoric moiety
reacting the ionophoric moiety with the alkali ion present in the sample, wherein the luminophoric moiety changes its luminescence properties,
measuring the luminescence and
determining the presence of the alkali ion in the sample utilizing the measured luminescence, wherein the compound is a monoaza-crown ether of the general Formula I

(I)

in which x is the luminophoric moiety, m is one selected from the group consisting of 0, 1 or 2, and r and s independently are selected from the group consisting of 0, 1 or 2.

2. Method according to claim 1 wherein r is 1 and s is 0.

3. Method according to claim 1 wherein r is 2 and s is 1.

4. Method according to any one of claims 1, 2 or 3 wherein x is selected from the group consisting of an amino-naphthalimide group and a xanthenone group wherein the amino-naphthalimide group has the general Formula II (II)

wherein at least one of $R_1$, $R_2$, $R_3$, $R_4$, $R_5$ and $R_6$ is an —NH— group through which x is bound to the group —$(CH_2)_m$— and the remaining groups and $R_7$ independently are selected from the group consisting of hydrogen, a lipophilic group, a hydrophilic group and a reactive group for coupling to a polymer and the xanthenone group has the general Formula III (III)

wherein m is o and at least one of $R_8$, $R_9$, $R_{10}$, $R_{11}$, $R_{12}$, $R_{13}$, $R_{14}$ and $R_{15}$ represents a chemical bond through which x is bound directly to the ionophoric moiety and the remaining groups are each selected from the group consisting of —OH, $OR_{16}$ wherein $R_{16}$ is a hydrophilic or a lipophilic group, —O—$R_{17}$—G wherein $R_{17}$ is a hydrophilic or a lipophilic group and G is a reactive group for coupling to a polymer, and —$(CH_2)n$—COOH wherein n is a number between 0 and 17.

5. Monoaza-crown ether of the general Formula I (I)

wherein x is a luminophoric moiety and m is selected from the group consisting of 0, 1, and 2, and r and s independently are selected from the group consisting of 0, 1 and 2.

6. Monoaza-crown ether in accordance with claim 5 wherein x is a luminophoric moiety as set forth in claim 4.

* * * * *

UNITED STATES PATENT AND TRADEMARK OFFICE
CERTIFICATE OF CORRECTION

PATENT NO. : 5,952,491

DATED : September 14, 1999

INVENTOR(S) : Leiner et al.

Page 1 of 3

It is certified that error appears in the above-indentified patent and that said Letters Patent is hereby corrected as shown below:

IN THE CLAIMS:

Column 11, line 7: "moiety" should read -- moiety, --;

Amendment A, claim 1, line 3

Column 11, line 10: "luminescence and" should read -- luminescence, and --; and

Amendment A, claim 1, lines 6-7

Column 12, line 4: "polymer and" should read -- polymer, and --.

Amendment A, claim 4, line 9

IN THE SPECIFICATION:

Column 3, line 5: "f.i." should read -- e.g., --;

Specification: page 3, line 22

Column 3, line 9: "f.i." should read -- e.g., --;

Specification: page 3, line 26

Column 4, line 5: "f.i." should read -- e.g., --;

Specification: page 5, line 4

Column 4, line 8: "f.i." should read -- e.g., --;

Specification: page 5, line 7

UNITED STATES PATENT AND TRADEMARK OFFICE
CERTIFICATE OF CORRECTION

PATENT NO. : 5,952,491

DATED : September 14, 1999

INVENTOR(S) : Leiner et al.

Page 2 of 3

It is certified that error appears in the above-indentified patent and that said Letters Patent is hereby corrected as shown below:

Column 4, line 12: "f.i." should read -- e.g., --;   Specification: page 5, line 9

Column 4, line 15: "f.i." should read -- e.g., --;   Specification: page 5, line 11

Column 4, line 16: "f.i." should read -- e.g., --;   Specification: page 5, line 12

Column 4, line 25: "f.i." should read -- e.g., --;   Specification: page 5, line 17

Column 5, line 22: "or2." should read -- or 2. --;   per Specification: page 5, line 22

Column 6, line 60: "f.i." should read -- e.g., --;   Specification: page 8, line 10

Column 8, line 19: "3.68g" should read -- 3.68g --;   per Specification: page 10, line 13

UNITED STATES PATENT AND TRADEMARK OFFICE
CERTIFICATE OF CORRECTION

PATENT NO. : 5,952,491
DATED : September 14, 1999
INVENTOR(S) : Leiner et al.

It is certified that error appears in the above-indentified patent and that said Letters Patent is hereby corrected as shown below:

Column 9, line 20: "chloroforn/methanol" should read -- per Specification: page 12, line 7 -- chloroform/methanol --;

Signed and Sealed this

Seventeenth Day of April, 2001

Attest:

NICHOLAS P. GODICI

*Attesting Officer*    *Acting Director of the United States Patent and Trademark Office*